US00PP09668P

United States Patent [19]

Dehan

[11] Patent Number: Plant 9,668

[45] Date of Patent: Oct. 22, 1996

[54] IMPATIENS PLANT NAMED 'MICKY GINI'

[75] Inventor: Klara Dehan, Holon, Israel

[73] Assignee: Danziger - "Dan" Flower Farm, Post Beit Dagan, Israel

[21] Appl. No.: 299,618

[22] Filed: Sep. 2, 1994

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—Foley & Lardner

[57] ABSTRACT

A new and distinct cultivar of Impatients plant named Micky Gini, characterized by its very small dark green leaves and small flowers, with the flowers standing well above the leaves, pink flower color with a white center eye; excellent self-branching and compact growth habit, and its very early flowering.

1 Drawing Sheet

The present invention relates to a new and distinctive cultivar of Impatiens plant, botanically known as Impatiens, commercially known as New Guinea impatiens, and known by the cultivar name Micky Gini.

The new cultivar was developed by the inventor Klara Dehan in Mishmar Hashiva, Israel in a controlled breeding program. The female or seed parent was a cultivar identified by the breeding number MC 5100, and the male or pollen parent was a cultivar identified by the breeding number MC 5141. Both parents are proprietary cultivars used in the breeding program. The new cultivar was selected by the inventor from the progeny of the stated cross.

Asexual reproduction of the new cultivar by leaf cuttings performed by the inventor in Mishmar Hashiva, Israel has established that the unique features of this new impatiens are stabilized and are reproduced true to type in successive propagations.

The following characteristics in combination distinguish the new impatiens Micky Gini from both its parent varieties and other cultivated Impatiens of this type known and used in the floriculture industry.

1. The primary distinguishing features are the relatively small flowers and the small leaves, with the flowers standing well above the leaves on long pedicels.
2. The flowers are pink with a white center eye.
3. The small leaves are dark green in color.
4. Excellent self-branching.
5. The cultivar is compact in growth habit and particularly suitable for small pots 7–10 cm in diameter.
6. The cultivar can be propagated by leaf cuttings year around.
7. Floriferous habit, with flowering being early and continuous.

The accompanying color photographic drawing illustrates the overall appearance of the cultivar, with the colors being as true as it is reasonably possible to obtain in a colored reproduction of this type. The flower color of the new cultivar is reasonably accurately illustrated. The color values described below are accurate.

The following is a detailed description of the new impatiens cultivar based on plants produced under commercial practice in Mishmar Hashiva, Israel. The plants described were grown in a net-covered greenhouse during the summer season with temperatures ranging from 35° C. maximum to 18° C. minimum. Color references are made to The Royal Horticultural Society Colour chart except where general terms of ordinary dictionary significance are used.

Parentage: The female parent MC 5100 and the male parent MC 5141 are seedlings from breeding program.

Propagation:

*Type cutting.*—Leaf cuttings.

*Time to initiate roots.*—7–8 days at 25° C. in summer; 8–9 days at 20° C. in winter.

*Rooting habit.*—Roots well.

Plant description:

*Form.*—Excellent self-branching produces a full, rounded symmetrical plant.

*Habit of growth.*—Compact growth habit, cultivar particularly suited for small pots 7–10 cm in diameter.

*Foliage.*—Size: Small; mature leaves 7.0 cm long and 3.0 cm wide. Shape: Lanceolate to ovate. Margin: Serrated. Color: Young and mature foliage, top side 147A; under side 147B. Venation: Green.

Flowering description:

*Flowering habits.*—The initiation of flower buds takes about 5–6 weeks from potting leaf cutting. Flowering is early, with flowers being completely open approximately 7–8 weeks after potting.

*Natural flowering season.*—The new cultivar flowers under ambient conditions in Israel all year, but in the winter season with less light, there are fewer flowers.

*Flower buds.*—Buds before opening are approximately 2.0 cm in length and 1.5 cm in width. Length of spur is 4 cm, and color is 46A. The spur does not take on a pink color progressively with flower maturity. Length of pedicel is 4.0 cm, with flowers standing above the foliage.

*Flowers borne.*—Flowers are carried on relatively long and sturdy pedicels and are fully open from initiation in about 2 weeks. Flowering continues all season.

*Quantity of flowers.*—Very floriferous, with 30–35 flowers open at the same time; long pedicels and floriferous habit produce a continuous abundance of flowers open above the leaves.

*Petals.*—Shape: Two (2) pairs of heart-shaped petals and a single larger petal; petals overlap. Color: Top side when opening 55A, with slight fading; under side 55B, with basal portions of the petals being white to provide a white eye. Number of petals: Five (5). Size of flowers: Small, about 4.0–4.5 cm in diameter.

*Reproductive organs.*—Stamens: One (1) in number. Anthers: Round, light red in color. Pollen color;

White. Pistils: Stigma: Round in shape, nearly white in color. Ovaries: Four (4) in number, 1 mm in size; light green in color.

Disease resistance: No significant disease problem noted to date.

I claim:

1. A new and distinct cultivar of Impatiens plant named Micky Gini, as illustrated and described.

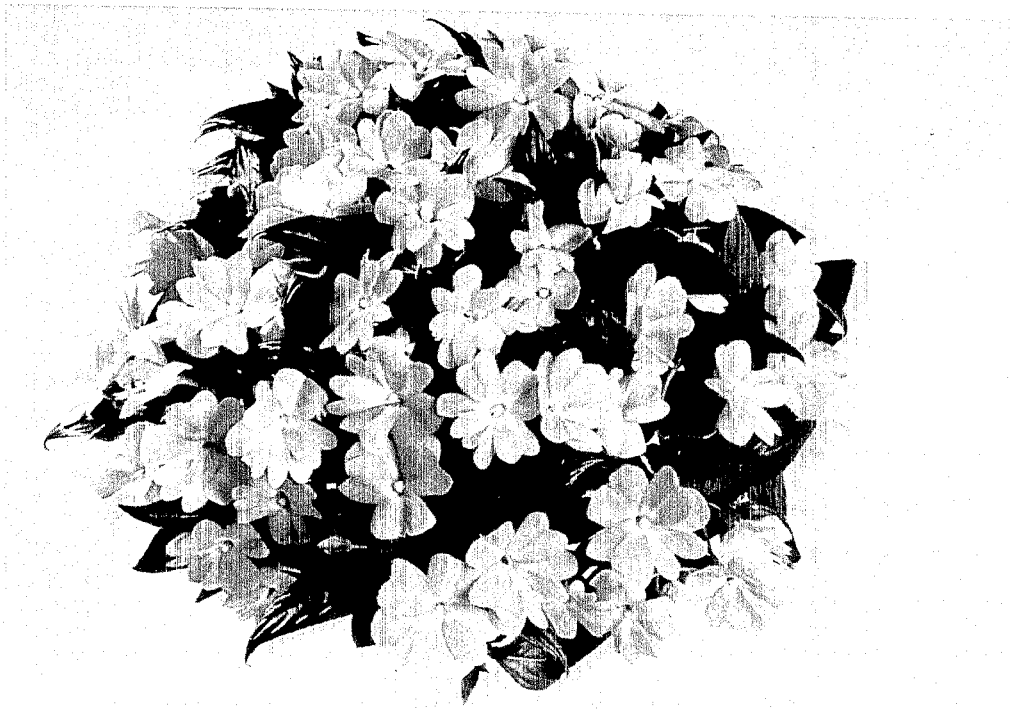

* * * * *